United States Patent [19]

Schäpertöns et al.

[11] Patent Number: 5,273,006

[45] Date of Patent: Dec. 28, 1993

[54] DEACTIVATABLE VALVE CONTROL ARRANGEMENT FOR INTERNAL COMBUSTION ENGINES

[75] Inventors: Herbert Schäpertöns, Gifhorn; Panagiotis Adamis, Wolfsburg; Joachim Neumann, Brunswick, all of Fed. Rep. of Germany

[73] Assignee: Volkswagen AG, Wolfsburg, Fed. Rep. of Germany

[21] Appl. No.: 32,973

[22] Filed: Mar. 18, 1993

[30] Foreign Application Priority Data

Mar. 30, 1992 [DE] Fed. Rep. of Germany ....... 4210322

[51] Int. Cl.⁵ .......................... F01L 1/34; F01L 1/18; F01L 1/26
[52] U.S. Cl. ................................ 123/90.16; 123/90.39
[58] Field of Search ............... 123/90.15, 90.16, 90.18, 123/90.17, 90.27, 90.39, 90.41, 90.44

[56] References Cited

U.S. PATENT DOCUMENTS

| | | | |
|---|---|---|---|
| 4,182,289 | 1/1980 | Nakajima et al. | 123/90.16 |
| 4,253,434 | 3/1981 | Takizawa et al. | 123/90.16 |
| 4,353,334 | 10/1982 | Neitz | 123/90.16 |
| 4,429,853 | 2/1984 | Chaffiotte et al. | 123/90.16 |
| 4,448,156 | 5/1984 | Henault | 123/90.18 |
| 4,584,974 | 4/1986 | Aoyama et al. | 123/90.16 |
| 4,768,475 | 9/1988 | Ikemura | 123/90.16 |
| 4,777,914 | 10/1988 | Konno | 123/90.16 |
| 4,788,946 | 12/1988 | Inoue et al. | 123/90.16 |
| 4,799,463 | 1/1989 | Konno | 123/90.16 |
| 5,101,778 | 4/1992 | Fukuo et al. | 123/90.16 |

FOREIGN PATENT DOCUMENTS

| | | |
|---|---|---|
| 3519471 | 1/1986 | Fed. Rep. of Germany . |
| 3526542 | 2/1986 | Fed. Rep. of Germany . |
| 3701609 | 8/1987 | Fed. Rep. of Germany . |
| 3735998 | 5/1988 | Fed. Rep. of Germany . |

*Primary Examiner*—E. Rollins Cross
*Assistant Examiner*—Weilun Lo
*Attorney, Agent, or Firm*—Brumbaugh, Graves, Donohue & Raymond

[57] ABSTRACT

A valve control arrangement for first and second inlet valves of an internal combustion engine includes two cams, one of which is optimized for operation at low speed and/or load, while the other cam is optimized for operation at high speed and/or load. The first valve is permanently driven and, when the second valve is deactivated, it is driven from the first cam by a first actuation lever. The second valve is driven by a second actuating lever after engagement actuation of a first coupling between the second actuation lever and a third actuating lever which is driven by the second cam. Another coupling between the first and second actuating levers couples the first valve with the second cam when required for optimum operation.

8 Claims, 1 Drawing Sheet

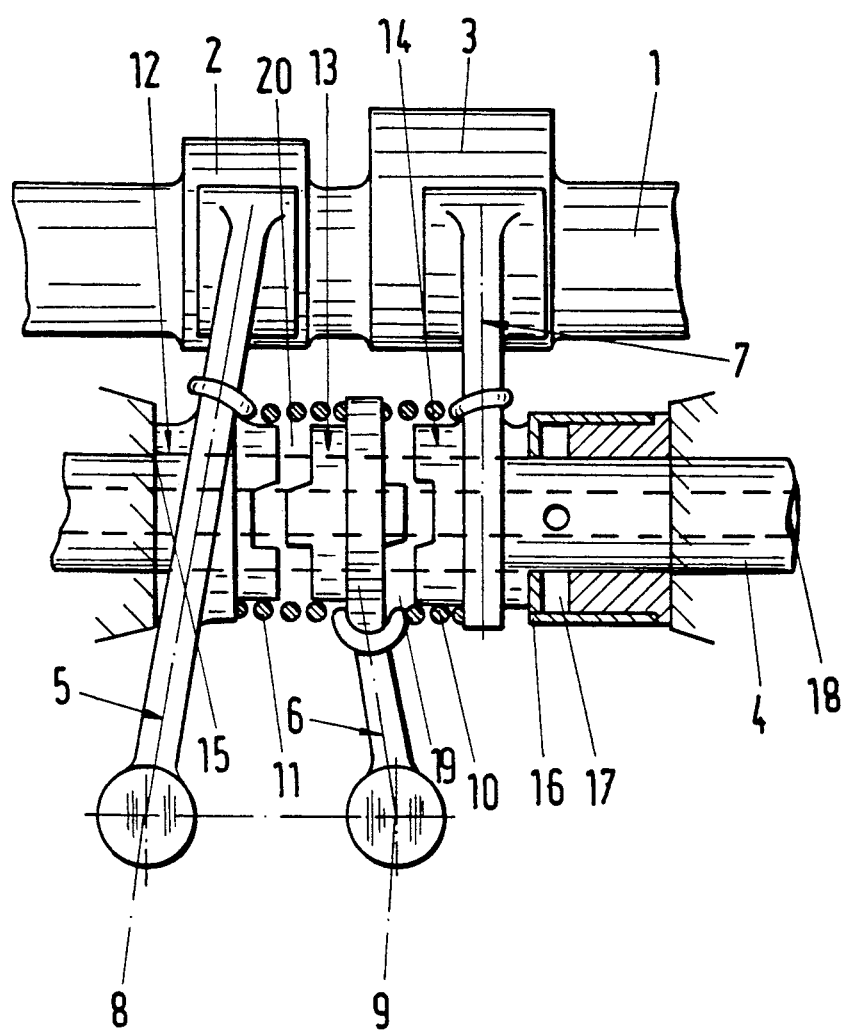

DEACTIVATABLE VALVE CONTROL ARRANGEMENT FOR INTERNAL COMBUSTION ENGINES

BACKGROUND OF THE INVENTION

This invention relates to control arrangements for deactivatable valves for internal combustion engines.

German Offenlegungsschrifts Nos. 35 19 471 and 37 01 609 and German Patent No. 3 526 542 disclose various arrangements for controlling the operation of deactivatable valves in internal combustion engines. For example, they provide the advantageous possibility of maintaining individual inlet valves closed at low engine speeds and loads so that the change of cylinder gases will take place through only some of the inlet valves. This can improve the after-charge effects because of the corresponding reduction of the cylinder inflow cross-sectional area.

In the designs disclosed in the first two references mentioned above, a single cam on the camshaft is provided for actuating both valves, that is, both a regularly actuated valve and a valve which may be maintained closed or actuated when appropriate. For this purpose, the valve-actuating levers for the two valves can be connected to each other, for example, by hydraulic pressure operating on a coupling arranged between the valve-actuating levers. This pressure produces a relative axial displacement of the bearing portions of the two actuating levers on the shaft so as to bring them into engagement.

The operation of the valve-actuating mechanism according to German Patent No. 3 526 542 is exactly the same in principle, but the coupling is of a configuration such that there is no relative sliding motion between the two actuating levers, and the coupling and release of the two transmission levers from each other is effected by axial motion of a piston which is eccentric to the shaft. Because only small pressure areas are available, this alternative requires high-pressure hydraulics.

Conventional engines are limited to merely activating and deactivating individual valves. Additional enhancements of torque and output of the engine could be achieved if the control times of the valves were also variable as functions of operating parameters of the engine, such as the rotational speed and load. On this point, Germany Offenlegungsschrift No. 37 35 998 discloses a valve-actuating mechanism having three cams on one camshaft and three actuating levers which are also capable of being selectively coupled and released by a piston-and-pin coupling. Since the central cam is designed for a greater travel than the other two cams, in the case of engagement actuating of the coupling described, it controls the displacement of all three valves when their actuation levers are coupled. Otherwise, the displacement of each valve is controlled by the cam individually assigned to it. In other words, this arrangement, while providing the possibility of selecting from several different valve control times, does not permit deactivation of individual valves.

SUMMARY OF THE INVENTION

Accordingly, it is an object of the present invention to provide a deactivatable valve control arrangement for internal combustion engines which overcomes the above-mentioned disadvantages of the prior art.

Another object of the invention is to provide a valve control arrangement for internal combustion engines that provides for both deactivation of individual valves and variation of valve control times as functions of engine parameters.

These and other objects of the invention are attained by providing a valve control arrangement for an internal combustion engine having at least two inlet or outlet lift valves to be controlled according to operating conditions including an actuating lever support shaft, a first actuating lever for actuating a first valve by a first cam, a second actuating lever mounted on the actuating lever support shaft for actuation of a second valve, a third actuating lever supported on the actuating lever support shaft and engaging a second cam providing greater cam-follower travel than the first cam, and a coupling arrangement operable as a function of at least one operating parameter of the engine including a first coupling for detachably connecting the second and third levers and a second coupling for detachably connecting the first and second levers in a predetermined sequence with respect to the operation of the first coupling. This arrangement thus provides for the possibility of driving a first permanently-actuated valve by way of the first actuating lever from the first cam while the second valve is deactivated at low engine load or speed so that the first cam can be optimized for those conditions. With increasing engine load and/or speed, the second valve can be actuated from the second cam, which may be optimized for high speed and/or load by sequential or simultaneous engagement of the first and second disengageable couplings to couple the first and second valve levers with the second cam. In this way, the permanently actuated first valve is also actuated from the second cam, which has a greater travel. Thus, it is possible to activate the second valve by engaging the second coupling to couple the second valve lever to the first actuation mechanism and then to change the actuation of both valves from the first cam to the second cam by engaging the first coupling. Alternatively, the second valve may first be actuated by engaging the first coupling first and then engaging the second coupling. Finally, it may also be expedient to engage both couplings simultaneously.

BRIEF DESCRIPTION OF THE DRAWING

Further objects and advantages of the invention will be apparent from a reading of the following description in conjunction with the accompanying drawing which is a schematic plan view, partly in section, illustrating a representative embodiment of a deactivatable valve control arrangement according to the invention.

DESCRIPTION OF PREFERRED EMBODIMENT

As will be apparent from the following description, one of the advantages of the present invention is that it can be embodied in a simple and therefore rugged construction.

The internal combustion engine with which the valve control arrangement of the invention is used has a conventional construction and therefore need not be described or illustrated. The typical valve control arrangement according to the invention, as shown in the drawing, includes a camshaft 1 having a first cam 2 and second cam 3 which is designed for greater cam-follower travel than the first cam 2. Parallel to the camshaft 1, which is driven by the engine in the conventional manner, is a lever support shaft 4, on which three actuating levers 5, 6 and 7 are pivotally mounted. These are referred to herein as the first, second and third actuating levers, respectively. The first actuating lever 5, which has the configuration of a bell crank, transmits actuating motions to a first intake valve positioned on an axis 8 to provide first valve operation which is optimized for low speed and/or load when in the condition shown in the drawing. This first valve is actuated under all operating conditions of the engine.

The additional actuating levers 6 and 7 are of a pivot lever configuration in contrast to the bell crank configuration of the lever 5. The second actuating lever 6 is arranged to transmit actuating forces to a second intake valve positioned on an axis 9. Both the first and second intake valves 8 and 9 are lift valves raised against the urging of corresponding valve-closing springs (not shown). Two coil springs 10 and 11, positioned around the lever support shaft 4, are coupled to the three actuating levers 5, 6 and 7 by terminal portions which are bent into hooks. In the condition shown in the drawing, the actuating lever 5 continuously engages the first cam 2 and the third actuating lever 7 continuously engages the second cam 3, whereas the second actuating lever 6 engage the stem of the valve on the axis 9 or a cup plunger coupled to that valve.

All of the actuating levers 5, 6 and 7 are pivotally mounted on the shaft 4 by hollow cylindrical bearing portions 12, 13 and 14, and the two actuating levers 6 and 7 are also axially displaceable on the shaft 4. One side of the cylindrical bearing portion 12 engages a stop 15 mounted on the shaft, while the cylindrical bearing portion 14 is axially adjacent to an actuating ring 16 which forms a boundary wall of an annular cylinder 17. The cylinder 17 is arranged to be supplied with a hydraulic pressure medium through a passage arrangement 18 in the shaft 4. When the hydraulic pressure applied to the annular cylinder 17 is increased, the actuating ring 16 is displaced to the left as seen in the drawing against the urging of the coil springs 10 and 11 in the axial direction.

The bearing portions 12, 13 and 14 have complementary jaws and recesses formed in their facing surfaces, forming a first coupling 19 between the two actuating levers 6 and 7 and a second coupling 20 between the actuating levers 5 and 6.

In the condition shown in the drawing, it is assumed that the pressure in the annular cylinder 17 is comparatively low so that the pressure of the springs 10 and 11 holds the couplings 19 and 20 in the uncoupled condition. Accordingly, the first valve 8, as previously mentioned, is driven by the first cam 2 and, although the third actuating lever 7 is pivoted by the second cam 3, there is no transmission of force to the second valve 9 because the first coupling 19 is disengaged. The second valve is therefore deactivated.

As soon as the pressure in the annular cylinder 17 is increased, the actuating ring 16 is able to displace at least the third actuating lever 7 to the left as seen in the drawing against the force of at least one of the springs 10 and 11 so that at least one of the couplings 19 and 20 will be moved into its engaged position. During this motion, the end of the actuating lever 7 will slide on the cam 3, which is made relatively wide to maintain engagement with the actuating lever during such motion. Assuming, by way of example, that initially, because of a weaker design of the spring 10, the first coupling 19 is engaged to make a connection between the two actuating levers 6 and 7, then the first valve 8 is actuated by the first cam 2 as before, but in addition the second valve 9 is actuated by the second cam 3. Upon a further increase of the pressure in the annular space 17 and consequent to further motion of the actuating ring 16 and the third actuating lever 7 to the left as seen in the drawing, the force of the spring 11 is also overcome and the coupling 20 is engaged to transmit torque between the first and second actuating levers. As a result, the first actuating lever 5, and hence the first valve 8, are also driven by the second cam 3.

By providing an oblique configuration of one flank of each of the coupling jaws in the couplings 19 and 20, an automatic elimination of play in those couplings, which might result from wear, is effected.

The invention thus provides a valve control arrangement for an internal combustion engine in which both activation and deactivation of individual valves and variation of valve control times are possible with a single structure.

Although the invention has been described herein with reference to a specific embodiment, many modifications and variations therein will readily occur to those skilled in the art. Accordingly, all such variations and modifications are included within the intended scope of the invention.

We claim:

1. A valve control arrangement for an internal combustion engine including at least one pair of inlet and outlet lift valves to be controlled according to operating conditions comprising a camshaft, a first cam mounted on the camshaft, a second cam mounted on the camshaft providing greater camfollower travel than the first cam, an actuating lever support shaft, a first actuating lever pivotally mounted on the actuating lever support shaft and being displaceable thereon in an axial direction of the lever support shaft to lockingly engage another actuating lever for actuation of a first valve by the first cam, a second actuating lever pivotally mounted on the lever support shaft for actuation of the second valve, a third actuating lever pivotally supported on the lever support shaft and engaging the second cam, and coupling means operable as a function of at least one operating parameter of the engine including a first coupling for detachably connecting the second and third actuating levers and a second coupling for detachably connecting the first and second actuating levers in a predetermined sequence with respect to the operation of the first coupling.

2. A valve control arrangement according to claim 1 wherein the operation of the second coupling to engage the first and second actuating levers takes place after the operation of the first coupling to engage the second and third actuating levers.

3. A valve control arrangement according to claim 1 wherein each of the first and second couplings includes complementary jaw and recess portions opposed to each other on the actuating levers which are displaceably mounted on the actuating lever support shaft and compression spring means connected between each adjacent pair of actuating levers.

4. A valve control arrangement according to claim 3 wherein the compression spring means includes springs which are configured and arranged as hold-down springs for the actuating levers.

5. A valve control arrangement according to claim 3 wherein the compression spring means includes springs of different strengths to provide sequential actuation of the first and second couplings.

6. A valve control arrangement according to claim 3 wherein the actuating levers have bearing portions on the support shaft which are disposed between a stop mounted on the lever support shaft and an axially displaceable actuating ring.

7. A valve control arrangement according to claim 6 including hydraulic drive means for displacing the actuating ring.

8. A valve control arrangement according to claim 1 wherein the first actuating lever is a bell crank and the second and third actuating levers are pivot levers.

* * * * *

UNITED STATES PATENT AND TRADEMARK OFFICE
CERTIFICATE OF CORRECTION

PATENT NO. : 5,273,006
DATED : December 28, 1993
INVENTOR(S) : Schäpertöns et al.

It is certified that error appears in the above-identified patent and that said Letters Patent is hereby corrected as shown below:

Title page Item [75], third line, "Brunswick" should read --Braunschweig--;

Column 3, line 23, "engage" should read --engages--;

Column 4, lines 35-37, delete "and being displaceable thereon in an axial direction of the lever support shaft to lockingly engage another actuating lever";

Column 4, line 39, after "shaft" insert --and being displaceable thereon in an axial direction of the lever support shaft to lockingly engage another actuating lever--.

Signed and Sealed this

Fifteenth Day of November, 1994

Attest:

BRUCE LEHMAN

Attesting Officer   Commissioner of Patents and Trademarks